US005814659A

United States Patent [19]
Elden

[11] Patent Number: 5,814,659
[45] Date of Patent: Sep. 29, 1998

[54] TOPICAL ANALGESIC COMPOSITION

[75] Inventor: Harry Richardson Elden, Miami, Fla.

[73] Assignee: DTR Dermal Therapy (Barbados) Inc., Bridgetown, Barbados

[21] Appl. No.: 636,440

[22] Filed: Apr. 23, 1996

[51] Int. Cl.[6] .......... A61K 31/27; A61K 31/335; A61K 31/22; A61K 31/225

[52] U.S. Cl. .......... 514/452; 514/478; 514/479; 514/546; 514/547; 514/552; 514/625; 514/629; 514/380

[58] Field of Search .......... 514/478, 479, 514/546, 547, 552, 625, 629

[56] References Cited

U.S. PATENT DOCUMENTS 5,482,965  1/1996  Rajadhyaksha et al. .

OTHER PUBLICATIONS

Kling, J.W. and Riggs, L.A., Editors, Woodworth & Schlosberg's *Experimental Psychology*, 3rd. edition, pp. 154–166, Holt, Rinehart and Winston, Inc., New York, N.Y. (1971).

Anchordoguy, T.J. et al., Effects of Protein Perturbants on Phospholipid Bilayers, *Arch. Biochem. Biophys.* 283: 356 (1990).

Behl, C.R. et al. Age and Anatomical Site Influence on Alkanol Permeation of Skin of the Male Hairless Mouse, *J. Soc. Cosmet. Chem.*, 35: 237 (1984).

Rowe, E.S., Lipid Chain Length and Temperature Dependence of Ethanol–Phosphatidyl Choline Interactions, *Biochemistry* 22: 3299 (1983).

Chemical Abstracts AN 1993:160285, Wohlrab, Jan. 1992.

Chemical Abstracts AN 1989:13572,Mahjour et al., Jan. 1989.

Chemical Abstracts AN 1993:546514, Gaspulin et al., 1993.

*Primary Examiner*—Keith D. MacMillan
*Attorney, Agent, or Firm*—Testa, Hurwitz & Thibeault, LLP

[57] ABSTRACT

The present invention comprises a topical analgesic composition comprising an analgesic agent, an alcohol, a chaotropic agent and an unsaturated fatty acid. The composition is preferably in the form of a stable gel and may further comprise a pharmaceutically acceptable emulsifier, a pharmaceutically acceptable gelling and/or thickening agent, and a pharmaceutically acceptable preservative. The pH of the composition is adjusted to 7.5–8.0 by the addition of a pharmaceutically acceptable organic base, such as triethanolamine.

The invention also comprises a method for inducing topical analgesia. The composition is absorbed on an absorbent material, for example a cotton strip inserted into typical skin-wipe packet; brought in contact with the skin of a person in need of such an analgesia; and maintained in contact with the skin for a period of time sufficient to induce and maintain topical analgesia.

42 Claims, No Drawings

5,814,659

TOPICAL ANALGESIC COMPOSITION

FIELD OF THE INVENTION

The present invention relates to a topical analgesic composition. More specifically, this invention relates to a topical analgesic composition for use in minor interventions on the skin, particularly in blood sampling.

BACKGROUND OF THE INVENTION

Determination of glucose in the blood of diabetic patients is an important prerequisite for efficient therapy, and diabetics often perform the procedure themselves. A blood sample is typically drawn from a finger which is pierced with a lancet. This procedure is accompanied by physiological pain and, because it must be performed on a repetitive basis, an anticipatory anxiety may develop. Such an anxiety tends to aggravate the perception of pain, especially in children.

Delivery of medication by needle injection also inflicts pain. When injections are administered regularly, as in the case of insulin in diabetic patients, an anticipatory anxiety toward pain tends to further aggravate their medical condition.

Pain perception is a complex psychophysical process that can be modified by attitude, attention and suggestion. No other sensation depends as much on cognition and information processing as does pain. See, for example, Kling, J. W. and Riggs, L. A., Editors, Woodworth & Schlosberg's *Experimental Psychology*, 3rd. edition, Holt, Rinehart and Winston, Inc., New York, N.Y. (1971).

Use of analgesic compositions, therefore, must be considered within the treatment context. At the same time, the treatment context is a factor that must be taken into account when considering the pharmacology and physiology of analgesic ingredients.

Analgesic potency of a chemical agent is known to correlate with its solubility in lipids. Analgesia occurs when lipid structures in neurosensory cell membranes are disrupted by a dissolved analgesic agent. This early observation of Meyer [Meyer, H., *Arch. Exp. Pathol. Pharmakol.* 42: 109 (1899)] and Overton [Overton, E. *Studien über die Narkose augleich ein Betrag zür algemainen Pharmakologie*, Gustav Fischer, Jena, Germany (1901)] is a fundamental postulate in the theory of analgesia, and remains intact to the present day. A contemporary version of this model of analgesia proposes that an analgesic agent disturbs the structure and organization of lipids in neurosensory cell membranes.

A number of topical analgesic agents are known to produce satisfactory results in acceptably low concentrations when applied to mucous membranes. They act rapidly and the effects last over a period sufficient to provide a temporary relief of pain. However, their efficacy in skin applications so far has been much less satisfactory. This is because, in order to reach the dermis where skin sensory receptors are located, and to be dissolved in the lipid domain of neurosensory cell membranes, a topical analgesic agent must first penetrate dense stratum corneum, keratinized comeocytes and the restrictive epidermal cell layer barrier of the skin surface.

There is thus a need for a topical analgesic composition which provides a fast and reliable analgesia for minor interventions on the skin, particularly for blood sampling and administration of medication by injection. In patients who have to take blood samples or receive medication regularly, such as diabetics, such a composition might ameliorate the occurrence of anticipatory anxiety. The topical analgesic composition of the present invention can also provide a more prolonged analgesia necessary for repetitive blood sampling.

SUMMARY OF THE INVENTION

In one aspect, the present invention provides a topical analgesic composition comprising an analgesic agent in an amount sufficient to induce analgesia, in admixture with an alcohol, a chaotropic agent and an unsaturated fatty acid, in amounts sufficient to provide the composition with penetration enhancing properties.

In one embodiment, the composition comprises an analgesic agent selected from the group consisting of benzocaine, butamben picrate, dibucaine, dimethisoquin, diclonyne, lidocaine, pramoxine, tetracine, and pharmaceutically acceptable salts thereof. In a preferred embodiment, the topical analgesic agent is selected from the group consisting of benzocaine, lidocaine, and pharmaceutically acceptable salts thereof. In a particular embodiment, the topical analgesic agent is lidocaine hydrochloride.

In one embodiment, the composition comprises an alcohol selected from the group consisting of aliphatic alcohols having from 2 to 8 C-atoms in the alkyl chain, benzyl alcohol, and combinations thereof. In a preferred embodiment, the alcohol is selected from the group consisting of n-propanol and benzyl alcohol.

According to another embodiment, the alcohol is substituted for by a combination of alcohol and phenol.

In one embodiment, the composition comprises a chaotropic agent selected from the group consisting of urea, N-alkyl- or N,N-dialkyl-substituted ureas having from 6 to 9 C-atoms in the alkyl group, amides of formula $(R^2)_2N$—CO—$R^1$—$R^3$, wherein $9^1$ represents a chemical bond or an alkyl group having from 1 to 14 C-atoms and $R^2$ and $R^3$ are independently hydrogen atoms or methyl groups, dimethyl sulfoxide, and combinations thereof. In a preferred embodiment, the chaotropic agent is urea.

In one embodiment, the composition comprises an unsaturated fatty acid selected from the group consisting of oleic acid, linoleic acid, linolenic acid and combinations thereof. In a preferred embodiment, the unsaturated fatty acid is oleic acid.

In a further embodiment, the composition of the present invention comprises a pharmaceutically acceptable emulsifier. In a preferred embodiment, the emulsifier is a lecithin selected from the group consisting of di-substituted 1,2-glycero-3-phosphatidyl cholines with 14 to 24 C-atoms in saturated acyl side chains thereof, purified natural lecithins such as soybean or egg yolk lecithin, and mixtures thereof.

In a further embodiment, the composition of the present invention comprises a pharmaceutically acceptable gelling and/or thickening agent, in an amount sufficient to provide the composition with properties of a stable gel. In a preferred embodiment, the pharmaceutically acceptable gelling and/or thickening agent is selected from the group consisting of a vinyl polymer with active carboxyl groups, xantan gum, hydroxypropylmethyl cellulose, magnesium aluminum silicate, high molecular weight polyethylene glycol, and combinations thereof.

In a further embodiment, the composition of the present invention comprises a pharmaceutically acceptable preservative. In a preferred embodiment, the pharmaceutically acceptable preservative is selected from the group consisting of methyl paraben, propyl paraben, imidazolidinyl urea, tetradecyltrimethyl ammonium bromide (Cetrimide), sodium benzoate, thymol, and combinations thereof.

In another aspect, the present invention provides a method of providing topical analgesia. The method comprises providing the topical analgesic composition of the present invention, for example applied to a cotton strip and inserted into a typical skin-wipe packet; bringing the topical analgesic composition in contact with the skin of a person in need of such an analgesia; and maintaining the topical analgesic composition in contact with the skin for a period of time sufficient to induce and maintain topical analgesia.

Other features and advantages of the present invention will become apparent to a person skilled in the art from the following detailed description of the invention.

DETAILED DESCRIPTION OF THE INVENTION

The present invention comprises a topical analgesic composition comprising an analgesic agent, an alcohol, a chaotropic agent and an unsaturated fatty acid. The composition can be applied to a strip of absorbent material which acts as a reservoir for the composition. The strip is generally contained in a typical skin-wipe packet. During application of the analgesic composition, direct contact between the skin and the reservoir permits diffusion of active ingredients.

The analgesic agent is responsible for analgesia at the site of application. A number of topical agents are known in the art, such as benzocaine, butamben picrate, dibucaine, dimethisoquin, diclonyne, lidocaine, pramoxine, tetracine, or pharmaceutically acceptable salts thereof. In the composition of the present invention, the analgesic agent typically comprises from about 0.2 to about 20 percent by weight of the final composition. According to a preferred embodiment, the analgesic agent used is benzocaine, lidocaine, or a pharmaceutically acceptable salt thereof. In a particular embodiment, the analgesic agent comprises lidocaine hydrochloride, known to be effective when applied to mucous membranes at relatively low concentrations.

Skin differs from soft and moist mucous membranes in that it contains a dense stratum corneum of keratinized cells, as well as the epidermal cell layer. Both act to restrain the penetration of salts and polar and hydrophilic molecules. In order to be effective in topical applications to skin, an analgesic agent has to be supplemented with agents that increase the hydration of the skin. Agents that break up dense macromolecular and lipid-rich domains are known as chaotropic agents. In cosmetology, their activity is the basis for improved hydration and moisturization of otherwise rough, scaly and dry skin. Anchordoguy showed that alcohols, amides and urea act as chaotropic agents [Anchordoguy, T. J. et al., Effects of Protein Perturbants on Phospholipid Bilayers, *Arch. Biochem. Biophys.* 283: 356 (1990)].

In addition to being mild analgesic agents themselves, pharmaceutically acceptable alcohols have been shown to possess chaotropic properties and to increase penetration of topically applied agents. Penetration and chaotropic activity improve with increased length of the hydrophobic hydrocarbon chain. See, for example, Behl, C. R. et al. Age and Anatomical Site Influence on Alkanol Permeation of Skin of the Male Hairless Mouse, *J. Soc. Cosmet. Chem.*, 35: 237 (1984). According to a preferred embodiment of this invention, the composition comprises from about 5 to about 15 percent by weight of an alcohol selected from the group consisting of aliphatic alcohols having from 2 to 8 C-atoms in the alkyl chain, and aromatic alcohols such as benzyl alcohol. In a more preferred embodiment, the alcohol used is n-propanol or benzyl alcohol.

In a further embodiment, the alcohol used may be supplemented with phenol which acts both as a mild analgesic agent and as a preservative. According to this embodiment, the composition will comprise from about 5 to about 15 percent by weight of a combination of alcohol and phenol.

Urea, substituted ureas, amides and dimethyl sulfoxide are known chaotropic agents. Urea itself shows some lipid solubility as well. Of particular importance to this invention are the abilities of this class of compounds, particularly urea, to diffuse rapidly in aqueous solutions and to break up dense macromolecular domains of fibrous and globular proteins. A pharmaceutically acceptable chaotropic agent of this type plays an important role in facilitating penetration of the analgesic agent into the skin. In one embodiment, the composition of the present invention comprises from about 5 to about 10 percent by weight of a chaotropic agent selected from the group consisting of urea, N-alkyl- or N,N-dialkyl-substituted ureas having from 6 to 9 C-atoms in the alkyl group, amides of formula $(R^2)_2N—CO—R^1—R^3$ wherein $R^1$ represents a chemical bond or an alkyl group having from 1 to 14 C-atoms and $R^2$ and $R^3$ are independently hydrogen atoms or methyl groups, dimethyl sulfoxide and combinations thereof. In a particular embodiment, the chaotropic agent used is urea.

Penetration of the composition can be enhanced by the addition of unsaturated long chain fatty acids. Long chain unsaturated fatty acids act to open channels in the epidermal cell barrier by increasing hydration, moisturization and break-up of lipid-rich domains of the skin surface. The composition can comprise from about 1 to about 5 percent by weight of an unsaturated fatty acid selected from the group consisting of oleic acid, linoleic acid, linolenic acid and mixtures thereof. In a preferred embodiment, the unsaturated fatty acid used is oleic acid.

A pharmaceutically acceptable emulsifier can be used in order to improve the availability of the analgesic agent, which may have a limited miscibility with lipids. The emulsifier can further enhance the penetration by facilitating the emulsification with hydrophobic substances that make up the natural barrier of the skin—lipids, cholesterol and ceramides.

In addition to being a suitable emulsifier, phosphatidyl cholines, or lecithins, interact with alcohols and enhance their analgesic action. Using pure model systems, Rowe showed that ethanol disruption of lipid structures increases when the number of C-atoms in saturated acyl side chains of di-substituted 1,2-glycero-3-phosphatidyl choline increases from 14 to 21 [Rowe, E. S., Lipid Chain Length and Temperature Dependence of Ethanol-Phosphatidyl Choline Interactions, *Biochemistry* 22: 3299 (1983)].

Naturally occurring lecithins may be derived from a variety of sources (eg. soybeans, egg yolk), and generally represent mixtures in which substituents comprise various percentages of acids. In one example, soybean lecithin is defined as comprising 11.7% palmitic acid, 4.0% stearic acid, 8.6% palmitoleic acid, 9.8% oleic acid, 55.0% linoleic acid, 4.0% linolenic acid and 5.5% of $C_{20}$–$C_{22}$ acids. Encompassed within the scope of the present invention are both synthetic phosphatidyl cholines (eg. products supplied by Avanti, Birmingham, Ala.), and naturally occurring lecithins (eg. products supplied by American Lecithin, Danbury, Conn.).

In one embodiment of the present invention, therefore, the composition comprises from about 1 to about 5 percent by weight of a lecithin selected from the group consisting of di-substituted 1,2-glycero-3-phosphatidyl cholines with 14 to 24 C-atoms in saturated acyl side chains thereof, purified natural lecithins such as soybean or egg yolk lecithin, and mixtures thereof.

The composition of the present invention is typically used with a strip of absorbent material. In order to provide for the stability of the composition, to prevent migration of individual components within the absorbent material and to ensure that the composition remains in an intimate contact with the skin during the application, the composition of a preferred embodiment is prepared in the form of a stable gel. Pharmaceutically acceptable gelling and thickening agents that can be used are carboxypolymethylene (a vinyl polymer with active carboxyl groups, e.g. Carbopol™ 940 supplied by B. F. Goodrich), xantan gum (eg. a product supplied by Rhone-Poulenc, Inc. under the name of Rhodigel™), hydroxymethylpropyl cellulose (eg. a product supplied by the Dow Chemical Company under the name of Methocel™), Veegum™ (a hydrated magnesium aluminum silicate supplied by R. T. Vanderbilt, Inc.), PEG-400™ (a high molecular weight polyethylene glycol supplied by the Dow Chemical Company), and combinations thereof. According to a preferred embodiment of the invention, gelling agents used are Carbopol™ 940 and PEG-400™. The gel will preferably have the viscosity within the range of about 3 to about 6 Cps (Centipoises).

To ensure stability of the gel, the pH of the composition is adjusted to about 7.5 to 8.0 by the addition of a pharmaceutically acceptable organic base, for example triethanolamine.

In order to maintain desired properties over prolonged periods of time, the composition can be supplemented with a pharmaceutically acceptable preservative. Such preservatives are well known in the art and include methyl paraben, propyl paraben, imidazolidinyl urea, tetradecyl-trimethyl ammonium bromide (Cetrimide), sodium benzoate, thymol and mixtures thereof. According to one embodiment, preservatives used are methyl paraben, imidazolidinyl urea and tetradecyltrimethyl ammonium bromide (Cetrimide).

The following examples illustrate some of the preferred embodiments of the present invention.

EXAMPLE 1

Gel composition according to the present invention is prepared from the following ingredients:

|  | percent by weight |
|---|---|
| Lidocaine Hydrochloride | 4.00 |
| Urea | 10.00 |
| Carbopol 940 | 0.40 |
| Methyl paraben | 0.20 |
| Imidazolidinyl urea | 0.30 |
| Cetrimide (Tetradecyltrimethyl ammonium bromide) | 0.20 |
| PEG-400 (Carbowax) | 7.00 |
| N-Propanol | 7.00 |
| Lecithin | 1.00 |
| Oleic acid | 1.00 |
| Triethanolamine 99% | to pH 7.5–8.0 |
| Sterile deionized water | q.s. to 100.00 |

To prepare 100.00 g of the composition according to the present invention, 10.00 g of urea are dissolved in approx. 50 g of sterile deionized water, 0.40 g of Carbopol 940 are added and the mixture is stirred until uniform. 0.20 g of methyl paraben and 0.30 g of imidazolidinyl urea are added while stirring and heating the mixture to 65°–70° C. Stirring is continued until all Carbopol 940 is dispersed and hydrated and an uniform mixture is obtained.

In a separate vessel, 4.75 g of 99% triethanolamine are mixed with approx. 3 g of sterile deionized water, and the mixture obtained is added to the above mixture which has been cooled down to 45°–50° C. Stirring is again continued to obtain an uniform mixture.

In another separate vessel, 0.20 g of Cetrimide are dissolved in 7.00 g of N-propanol together with 7.00 g of PEG-400, 1.00 g of lecithin and 1.00 g of oleic acid, with slight heating. The solution is added to the above mixture under continuous stirring, again until an uniform mixture is obtained.

Finally, 4.00 g of lidocaine hydrochloride are dissolved in approx. 10 g of sterile deionized water, with slight heating, the solution is added to the above mixture, and stirring is continued until the mixture becomes uniform. The pH of the composition is adjusted to 7.5–8.0 with triethanolamine and deionized water is added to 100.00 g.

EXAMPLE 2

The composition according to the invention was prepared as described in Example 1, except in that lidocaine hydrochloride was replaced with an appropriate amount of lidocaine free base or benzocaine, respectively. The amounts of Carbopol 940, PEG-400, lecithin and water may be adjusted as required, to provide a stable gel with the viscosity of 3 to 6 Cps.

EXAMPLE 3

The composition according to the invention was prepared as described in Example 1, except in that n-propanol was replaced with an appropriate amount of benzyl alcohol. The amounts of Carbopol 940, PEG-400, lecithin and water may be adjusted as required, to provide a stable gel with the viscosity of 3 to 6 Cps.

EXAMPLE 4

The composition according to the invention was prepared as described in Example 2, except in that n-propanol was replaced with an appropriate amount of benzyl alcohol. The amounts of Carbopol 940, PEG-400, lecithin and water may be adjusted as required, to provide a stable gel with the viscosity of 3 to 6 Cps.

EXAMPLE 5

The composition according to the invention was prepared as described in Example 1, except in that n-propanol was replaced with an appropriate amount of ethanol, butanol, pentanol, hexanol, heptanol or octanol, respectively. The amounts of Carbopol 940, PEG-400, lecithin and water may be adjusted as required, to provide a stable gel with the viscosity of 3 to 6 Cps.

EXAMPLE 6

The composition according to the invention was prepared as described in Example 1, except in that urea is replaced with an appropriate amount of N-hexyl urea, N,N-dihexyl urea, N-dodecyl urea, N,N-didodecyl urea, acetamide, dimethyl acetamide, formamide, dimethyl formamide, dimethyl sulfoxide, N,N-dimethyl propylamide, N,N-dimethyl octylamide or N,N-dimethyl tetradecylamide, respectively. The amounts of Carbopol 940, PEG-400, lecithin and water may be adjusted as required, to provide a stable gel with the viscosity of 3 to 6 Cps.

EXAMPLE 7

The composition according to the invention was prepared as described in Example 1, except in that lecithin is replaced with an appropriate amount of alternative purified natural lecithin, with a synthetic di-substituted 1,2-diglycero-3-phosphatidyl choline having from 14 to 24 C-atoms in saturated acyl side chains, or with a mixture thereof. The amounts of Carbopol 940, PEG-400 and water may be adjusted as required, to provide a stable gel with the viscosity of 3 to 6 Cps.

EXAMPLE 8

The composition according to the invention was prepared as described in Example 1, except in that oleic acid was replaced with an appropriate amount of linoleic acid or linolenic acid, respectively. The amounts of Carbopol 940, PEG-400, lecithin and water may be adjusted as required, to provide a stable gel with the viscosity of 3 to 6 Cps.

EXAMPLE 9

The composition according to the invention was prepared as described in Example 5, except in that lidocaine hydrochloride was replaced with an appropriate amount of benzocaine. The amounts of Carbopol 940, PEG-400, lecithin and water may be adjusted as required, to provide a stable gel with the viscosity of 3 to 6 Cps.

EXAMPLE 10

The composition according to the invention was prepared as described in Example 9, except in that n-propanol was replaced with an appropriate amount a mixture of benzyl alcohol and phenol. The amounts of Carbopol 940, PEG-400, lecithin and water may be adjusted as required, to provide a stable gel with the viscosity of 3 to 6 Cps.

CLINICAL STUDIES

In order to assess the analgesic effects of the composition of the present invention, a number of studies has been conducted. In the following study, the effect of the composition on a non-occluded finger skin site was determined.

Test site was prepared by wiping finger with the cotton pad containing the composition of Example 1, site was pierced with a lancet, and again wiped with the pad. Pain was estimated by measuring number of probes judged painful per trial of 10, at zero time and at subsequent 5 minutes intervals. The data presented in Table 1 show that the perceived pain decreases rapidly after initial application of the composition. Quantification of the perceived pain is based on a 5-point VAS (visual analog scale), where 5=intense pain and 0=no pain.

TABLE 1

Estimation of Analgesia Based on Visual Analog Scale (VAS)
-Perceived Pain After Lancet Pricks-
VAS Scale 5 = Intense Pain; VAS Scale 0 = No Pain

| Elapsed Time (min.) | Response |
| --- | --- |
| 0 | 5.00 |
| 5 | 4.90 |
| 10 | 2.50 |
| 12 | 2.30 |
| 21 | 1.50 |
| 30 | 2.50 |
| 40 | 3.50 |
| 52 | 4.50 |
| 60 | 5.00 |

While in this specification the invention has been described in detail through an example of some of the preferred embodiments thereof, it will be obvious to a person skilled in the art that many variations and modifications could be made without departing from the scope and spirit of the present invention. Therefore, the present invention should be considered as limited only by the scope of the claims appended thereto.

What is claimed is:

1. A topical analgesic composition comprising:
    a topical analgesic agent in an amount sufficient to induce analgesia; and
    an alcohol, a chaotropic agent and an unsaturated fatty acid, in amounts sufficient to enhance penetration of the topical analgesic agent.

2. A topical analgesic composition according to claim 1, wherein the topical analgesic agent comprises from about 0.2 to about 20 weight percent of an agent selected from the group consisting of benzocaine, butamben picrate, dibucaine, dimethisoquin, diclonyne, lidocaine, pramoxine, tetracine, and pharmaceutically acceptable salts thereof.

3. A topical analgesic composition according to claim 2, wherein the topical analgesic agent is selected from the group consisting of benzocaine, lidocaine, and pharmaceutically acceptable salts thereof.

4. A topical analgesic composition according to claim 3, wherein the topical analgesic agent is lidocaine hydrochloride.

5. A topical analgesic composition according to claim 1, wherein the alcohol comprises from about 5 to about 15 weight percent of an alcohol selected from the group consisting of aliphatic alcohols having from 2 to 8 C-atoms in the alkyl chain, benzyl alcohol, and combinations thereof.

6. A topical analgesic composition according to claim 5, wherein the alcohol is selected from the group consisting of n-propanol and benzyl alcohol.

7. A topical analgesic composition according to claim 1, wherein the chaotropic agent comprises from about 5 to about 10 percent by weight of an agent selected from the group consisting of urea, N-alkyl- or N,N-dialkyl-substituted ureas having from 6 to 9 C-atoms in the alkyl group, amides of formula $(R^2)_2N-CO-R^1-R^3$ wherein $R^1$ represents a chemical bond or an alkyl group having from 1 to 14 C-atoms and $R^2$ and $R^3$ are independently hydrogen atoms or methyl groups, dimethyl sulfoxide, and combinations thereof.

8. A topical analgesic composition according to claim 7, wherein the chaotropic agent is urea.

9. A topical analgesic composition according to claim 1, wherein the unsaturated fatty acid comprises from about 1 to about 5 percent by weight of an acid selected from the group consisting of oleic acid, linoleic acid, linolenic acid and combinations thereof.

10. A topical analgesic composition according to claim 9, wherein the unsaturated fatty acid is oleic acid.

11. A topical analgesic composition according to claim 1, further comprising a pharmaceutically acceptable emulsifier.

12. A topical analgesic composition according to claim 11, wherein the pharmaceutically acceptable emulsifier comprises from about 1 to about 5 weight percent of a lecithin selected from the group consisting of di-substituted 1,2-diglycero-3-phosphatidyl cholines having from 14 to 21 C-atoms in saturated acyl side chains thereof, purified natural lecithins, and mixtures thereof.

13. A topical analgesic composition according to claim 1, further comprising a pharmaceutically acceptable gelling and/or thickening agent, in an amount sufficient to provide the composition with properties of a stable gel.

14. A topical analgesic composition according to claim 13, wherein the pharmaceutically acceptable gelling and/or thickening agent comprises from about 0.1 to about 10 weight percent of an agent selected from the group consisting of carboxypolymethylene, xantan gum, hydroxymethylpropyl cellulose, magnesium aluminum silicate, polyethylene glycol, and combinations thereof.

15. A topical analgesic composition according to claim 1, wherein the composition is in the form of a stable gel having viscosity of from about 3 to about 6 Cps.

16. A topical analgesic composition according to claim 1, further comprising a pharmaceutically acceptable preservative.

17. A topical analgesic composition according to claim 16, wherein the pharmaceutically acceptable preservative comprises from about 0.1 to about 1 weight percent of a pharmaceutically acceptable preservative selected from a group consisting of methyl paraben, propyl paraben, imidazolidinyl urea, tetradecyltrimethyl ammonium bromide (Cetrimide), sodium benzoate, thymol, and combinations thereof.

18. A topical analgesic composition according to claim 1, wherein pH of the composition is adjusted to from about 7.5 to about 8.0.

19. A topical analgesic composition according to claim 1, wherein the pH of the composition is adjusted by the addition of a pharmaceutically acceptable organic base.

20. A topical analgesic composition according to claim 19, wherein the pharmaceutically acceptable organic base is triethanolamine.

21. A topical analgesic composition according to claim 1, wherein the alcohol is substituted with a combination of alcohol and phenol.

22. A method of inducing topical analgesia, comprising:
providing a topical analgesic composition comprising a topical analgesic agent in an amount sufficient to induce analgesia; and an alcohol, a chaotropic agent and an unsaturated fatty acid, in amounts sufficient to enhance penetration of the topical analgesic agent;
bringing the topical analgesic composition in contact with the skin of a person in need of such an analgesia; and
maintaining the occlusive packet in contact with the skin for a period of time sufficient to induce and maintain topical analgesia.

23. A method according to claim 22, wherein the topical analgesic agent comprises from about 0.2 to about 20 weight percent of an agent selected from the group consisting of benzocaine, butamben picrate, dibucaine, dimethisoquin, diclonyne, lidocaine, pramoxine, tetracine, and pharmaceutically acceptable salts thereof.

24. A method according to claim 23, wherein the topical analgesic agent is selected from the group consisting of benzocaine, lidocaine, and pharmaceutically acceptable salts thereof.

25. A method according to claim 24, wherein the topical analgesic agent is lidocaine hydrochloride.

26. A method according to claim 22, wherein the alcohol comprises from about 5 to about 15 weight percent of an alcohol selected from the group consisting of aliphatic alcohols having from 2 to 8 C-atoms in the alkyl chain, benzyl alcohol, and combinations thereof.

27. A method according to claim 26, wherein the alcohol is selected from the group consisting of n-propanol and benzyl alcohol.

28. A method according to claim 22, wherein the chaotropic agent comprises from about 5 to about 10 percent by weight of an agent selected from the group consisting of urea, N-alkyl- or N,N-dialkyl-substituted ureas having from 6 to 9 C-atoms in the alkyl group, amides of formula $(R^2)_2N-CO-R^1-R^3$ wherein $R^1$ represents a chemical bond or an alkyl group having from 1 to 14 C-atoms and $R^2$ and $R^3$ are independently hydrogen atoms or methyl groups, dimethyl sulfoxide, and combinations thereof.

29. A method according to claim 28, wherein the chaotropic agent is urea.

30. A method according to claim 22, wherein the unsaturated fatty acid comprises from about 1 to about 5 percent by weight of an acid selected from the group consisting of oleic acid, linoleic acid, linolenic acid and combinations thereof.

31. A method according to claim 30, wherein the unsaturated fatty acid is oleic acid.

32. A method according to claim 22, wherein the composition further comprises a pharmaceutically acceptable emulsifier.

33. A method according to claim 32, wherein the pharmaceutically acceptable emulsifier comprises from about 1 to about 5 weight percent of a lecithin selected from the group consisting of di-substituted 1,2-diglycero-3-phosphatidyl cholines having from 14 to 21 C-atoms in saturated acyl side chains thereof, purified natural lecithins, and mixtures thereof.

34. A method according to claim 22, wherein the composition further comprises a pharmaceutically acceptable gelling and/or thickening agent, in an amount sufficient to provide the composition with properties of a stable gel.

35. A method according to claim 34, wherein the pharmaceutically acceptable gelling and/or thickening agent comprises from about 0.1 to about 10 weight percent of an agent selected from the group consisting of carboxypolymethylene, xantan gum, hydroxymethylpropyl cellulose, magnesium aluminum silicate, polyethylene glycol, and combinations thereof.

36. A method according to claim 22, wherein the composition is in the form of a stable gel having viscosity of from about 3 to about 6 Cps.

37. A method according to claim 22, wherein the composition further comprises a pharmaceutically acceptable preservative.

38. A method according to claim 37, wherein the pharmaceutically acceptable preservative comprises from about 0.1 to about 1 weight percent of a pharmaceutically acceptable preservative selected from a group consisting of methyl paraben, propyl paraben, imidazolidinyl urea, tetradecyltrimethyl ammonium bromide (Cetrimide), sodium benzoate, thymol, and combinations thereof.

39. A method according to claim 22, wherein pH of the composition is adjusted to from about 7.5 to about 8.0.

40. A method according to claim 22, wherein the pH of the composition is adjusted by the addition of a pharmaceutically acceptable organic base.

41. A method according to claim 40, wherein the pharmaceutically acceptable organic base is triethanolamine.

42. A method according to claim 22, wherein the alcohol is substituted with a combination of alcohol and phenol.

* * * * *